US008712132B2

(12) United States Patent
Bauer et al.

(10) Patent No.: US 8,712,132 B2
(45) Date of Patent: Apr. 29, 2014

(54) METHOD AND COMPUTER SYSTEM FOR AUTOMATIC VECTORIZATION OF A VESSEL TREE

(75) Inventors: Miriam Bauer, Braunfels (DE);
Thomas Beck, Forchheim (DE);
Dominik Bernhardt, Hausen (DE);
Christina Biermann, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 306 days.

(21) Appl. No.: 13/092,999

(22) Filed: Apr. 25, 2011

(65) Prior Publication Data

US 2011/0262020 A1 Oct. 27, 2011

(30) Foreign Application Priority Data

Apr. 26, 2010 (DE) .......................... 10 2010 018 261

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS

| 7,620,205 | B2 | 11/2009 | Comaniciu | |
|---|---|---|---|---|
| 7,912,270 | B2* | 3/2011 | Skinner et al. | 382/131 |
| 8,406,491 | B2* | 3/2013 | Gee et al. | 382/128 |
| 2007/0081712 | A1 | 4/2007 | Guan | |
| 2008/0085042 | A1 | 4/2008 | Hayam | |
| 2008/0118121 | A1* | 5/2008 | Skinner et al. | 382/128 |
| 2008/0159604 | A1 | 7/2008 | Ternovskiy | |
| 2009/0161937 | A1 | 6/2009 | Krishnan | |
| 2010/0159497 | A1* | 6/2010 | Kimia et al. | 435/29 |
| 2010/0296709 | A1* | 11/2010 | Ostrovsky-Berman et al. | 382/128 |
| 2010/0296718 | A1* | 11/2010 | Ostrovsky-Berman et al. | 382/133 |
| 2011/0040713 | A1* | 2/2011 | Colman et al. | 706/16 |
| 2011/0103667 | A1 | 5/2011 | Biermann et al. | |
| 2011/0262020 | A1* | 10/2011 | Bauer et al. | 382/131 |
| 2012/0155734 | A1* | 6/2012 | Barratt et al. | 382/131 |

FOREIGN PATENT DOCUMENTS

| DE | 102009032257 A1 | 1/2011 |
|---|---|---|
| WO | WO 2009017715 A1 | 2/2009 |

OTHER PUBLICATIONS

Proc. SPIE, vol. 4322, pp. 236-248, DOI: 10.1117/12.431093; Book; 2001.
German Priority document DE 102010018261.3.

* cited by examiner

*Primary Examiner* — Tahmina Ansari
(74) *Attorney, Agent, or Firm* — Harness, Dickey & Pierce, P.L.C.

(57) ABSTRACT

A method and a computer system are disclosed for automatic vectorization of the profile of a vessel tree and at least one of its properties on the basis of tomographic images of an examined patient. In at least one embodiment, using previously established location probabilities of landmarks in the vessel tree, there is an automatic determination of a plurality of distinctive landmarks in the current tomographic image data record of the patient, a registration of the current tomographic image data record to the statistical vessel model, an automatic determination of previously unidentified landmarks in the registered tomographic image data record using characteristic identification features of the previously unidentified landmarks from the statistical vessel model and the statistical location probability thereof, and a determination of at least one current vessel model using the identified landmarks and at least one vessel property at and/or between the identified landmarks.

16 Claims, 7 Drawing Sheets

METHOD AND COMPUTER SYSTEM FOR AUTOMATIC VECTORIZATION OF A VESSEL TREE

PRIORITY STATEMENT

The present application hereby claims priority under 35 U.S.C. §119 on German patent application number DE 10 2010 018 261.3 filed Apr. 26, 2010, the entire contents of which are hereby incorporated herein by reference.

FIELD

At least one embodiment of the invention generally relates to a method for automatic vectorization of the profile of a vessel tree and at least one of its properties on the basis of tomographic images of an examined patient. Moreover, at least one embodiment of the invention also relates to a computer system, in particular from a tomography system with a scanner, for image evaluation, comprising a storage medium for computer programs, which carry out at least one embodiment of the aforementioned method.

BACKGROUND

Within the scope of imaging methods in medicine, the practice of extracting tomographic image information from a patient for obtaining information therefrom in respect of physiological conditions in the examined patient and for providing this information to a medical practitioner for diagnostic purposes is well known. Thus, by way of example, a 3D data record of a vessel system is generated in CT angiography after the administration of a contrast agent; this 3D data record allows a medical practitioner to diagnose deformations of vessels such as stenoses or aneurysms. In principle, this diagnosis can be performed directly on the tomographic displays. For simplification, the medical practitioner can for example also be provided with a so-called curved multiplanar reconstruction (CPR) as an overview over a vessel in the vessel system; this is based on establishing the midline in the image of the vessel. The CPR can provide the medical practitioner with a first overview over the state of the observed vessel and e.g. can allow the positions for measuring the vessel to be established. The measurement of a vessel based on CPR requires substantially less time than the direct assessment of the tomographic image data records.

However, the continuous improvement in the image quality goes hand in hand with an increasing number of images to be diagnosed. The upshot of this is that the amount of time required for viewing the images per patient is ever increasing. Along with the increasing number of images to be assessed, the risk of overlooking pathologies in the large volume of information increases at the same time.

SUMMARY

In at least one embodiment of the invention, a medical practitioner is provided with an improved system that provides the essential data of present vessel structures in a concentrated form and thus allows a simpler and faster evaluation.

Advantageous developments of the invention are the subject matter of the dependent claims.

In at least one embodiment, the inventors have recognized the following:

Firstly, the automatic application of previously learnt anatomical knowledge in respect of the relative positioning of landmarks in a vessel tree and characteristic features of the vessel tree at and/or between these landmarks in a vectorized form allows an automatic identification procedure for a vessel tree to be carried out in a substantially more effective fashion; secondly, a medical practitioner can be provided with substantially more concentrated information in respect of the anatomical properties of the vessel tree by a vectorization of the extracted image data of the vessel tree required for this.

In principle, the basis for this vectorized identification and display of a vessel tree is the description of a vessel tree by a graph model, which consists of landmarks and vessel connections, a statistical vessel model, which consists of an application of the graph model to a multiplicity of previously established tomographic image data and a generation of statistical location probabilities, which describes the relative positioning of identified landmarks with respect to one another and statistical characteristic parameters of the vessel connections. Additionally, characteristic shapes of branchings at the landmarks may also be specified herein and can be used within the scope of pattern recognition. Finally, it is necessary to extract precisely this vessel model from the currently observed patient or their tomographic image data record. In the process, a few particularly striking landmarks are at first determined automatically, and a registration to the statistical vessel model is carried out on the basis of the positions of these landmarks. Now, the positions at which, or the region of the location probabilities in which, further landmarks known from the statistical vessel model should lie are known, and the pattern recognition can be restricted to these regions in a targeted fashion. This step alone drastically increases the recognition probability. Additionally, the information relating to characteristic shapes and sizes of the vessel tree at the respective landmarks may also be used; this respectively makes pattern recognition more reliable.

If not all of the landmarks were identified, there can be another or a number of iterative registration(s) using the landmarks of the statistical vessel model to the landmarks of the already identified vessel model, as a result of which the identification with the respectively registered data records is improved in each case.

In accordance with this basic idea, the inventors propose a method for automatic vectorization of the profile of a vessel tree and at least one of its properties on the basis of tomographic images of an examined patient, comprising at least the following method steps:

providing statistically established location probabilities of landmarks in a vessel tree, in the form of a statistical vessel model, on the basis of evaluated tomographic image data records from a multiplicity of statistically comparable persons, acquiring or generating a current tomographic image data record of the patient, automatically determining a plurality of distinctive landmarks in the vessel tree in the current tomographic image data record of the patient, registering the current tomographic image data record to the statistical vessel model by approximating the landmarks established in the current tomographic image data record with the corresponding landmarks in the statistical vessel model, automatically determining previously unidentified landmarks in the registered tomographic image data record using characteristic identification features of the previously unidentified landmarks from the statistical vessel model and the statistical location probability thereof, determining at least one current vessel model using the identified landmarks and at least one vessel property at and/or between the identified landmarks, outputting the current vessel model.

If not all of the landmarks present in the statistical vessel model were found in the first run-through of this method according to the invention, it is possible that at least one iteration is carried out with repeated registration using all known landmarks and identification of new landmarks. Interrupt criteria for this iterative procedure may be e.g. the number of iterations carried out, or the identification of all landmarks or a prescribed number of landmarks.

Additionally, the method according to at least one embodiment of the invention may also provide the user with the option of filtering the output data from the current vessel model. The filter criteria used in this may, firstly, be selected freely or be selected from a number of predefined filter criteria. More particularly, examined vessel properties may be used for filtering, such as e.g. vessel diameter, variance of the vessel diameter between two landmarks and/or vessel-wall thicknesses or the variance thereof.

In order to register the landmarks in the statistical vessel model to the currently found landmarks including the associated current tomographic image data record, use can be made in particular of the principle of an active shape model or an active appearance model. In respect of both models, reference is made in an example fashion to the article T. F. Cootes and C. J. Taylor, Statistical models of appearance image analysis and computer vision, Proc. SPIE Medical Imaging, 2001, the entire contents of which are hereby incorporated herein by reference, and to the further references cited therein.

The inventors furthermore propose the use of pattern recognition for identifying landmarks, which pattern recognition is restricted to the region with a predefined location probability of the sought-after landmark as per the statistical vessel model. As a result of this spatial restriction of the search, the probability of a hit and the efficiency of the pattern recognition is drastically increased compared to an untargeted search. In order to support this, it is also additionally possible to use statistically established basic shapes of the vessel tree, which is respectively the most likely at the sought-after landmark or which at least belongs to the basic shapes occurring with a relatively high probability.

According to at least one embodiment of the invention, the statistical vessel model can at least have information relating to the description of each landmark and the statistical position thereof as parameters.

Furthermore, the vessel model output on the basis of the current recording of a patient can contain, in addition to the landmark parameters, at least one parameter for the statistical description of the geometry of the vessel in each vessel section between two landmarks.

In addition to the above-described method, the scope of at least one embodiment of the invention also includes a computer system, in particular a computer system from a tomography system with a scanner, which computer system is at least used for image evaluation as well and comprises a storage medium for computer programs for this purpose, wherein, in the storage medium, there are also computer programs, optionally in addition to further evaluation and control programs, which carry out at least one method according to at least one embodiment of the invention during operation.

BRIEF DESCRIPTION OF THE DRAWINGS

In the following text, the invention will be explained in more detail on the basis of a preferred example embodiment with the aid of figures, with only the features required for understanding the invention being illustrated. The following reference signs are used: 1 to 119: landmark IDs; A: location probability; C1: CT-system/C-arm system; C2: first X-ray tube; C3: first detector; C4: second X-ray tube (optional); C5: second detector (optional); C6: CT-system scanner or C-arm system scanner; C7: C-arm; C8: patient couch; C9: system axis; C10: CT-system computer system or C-arm system computer system; C11: contrast-agent applicator; C12: EKG line; GA: vessel section; GM: graph model; L: landmark; M: profile of the midline of a vessel; M1: MRI (magnetic resonance imaging) system; M2: magnetic coils; M3: reception coils; M4: gradient coils; M6: MRI-system scanner; M10: MRI-system computer system; P: patient; $Prg_1$-$Prg_n$: computer programs; R: profile of statistical radii; S11 to S28: method steps, respectively with the following meaning: S11: start, S12: loading existing statistical vessel model, S13: generating empty statistical vessel model, S14: examined the volume of training data?, S16: extracting vessel model, S17: registering to statistical vessel model, S18: merging vessel models, S21: start, S22: defining a portion of contained landmarks, S23: registering to statistical vessel model, S24: detection of further landmarks, S25: further landmarks?, S26: extraction of the vessel model, S27: vessel model extended?, S28: vessel model generated; SG: statistical vessel model.

In detail.

DETAILED DESCRIPTION OF THE EXAMPLE EMBODIMENTS

Figure 1:
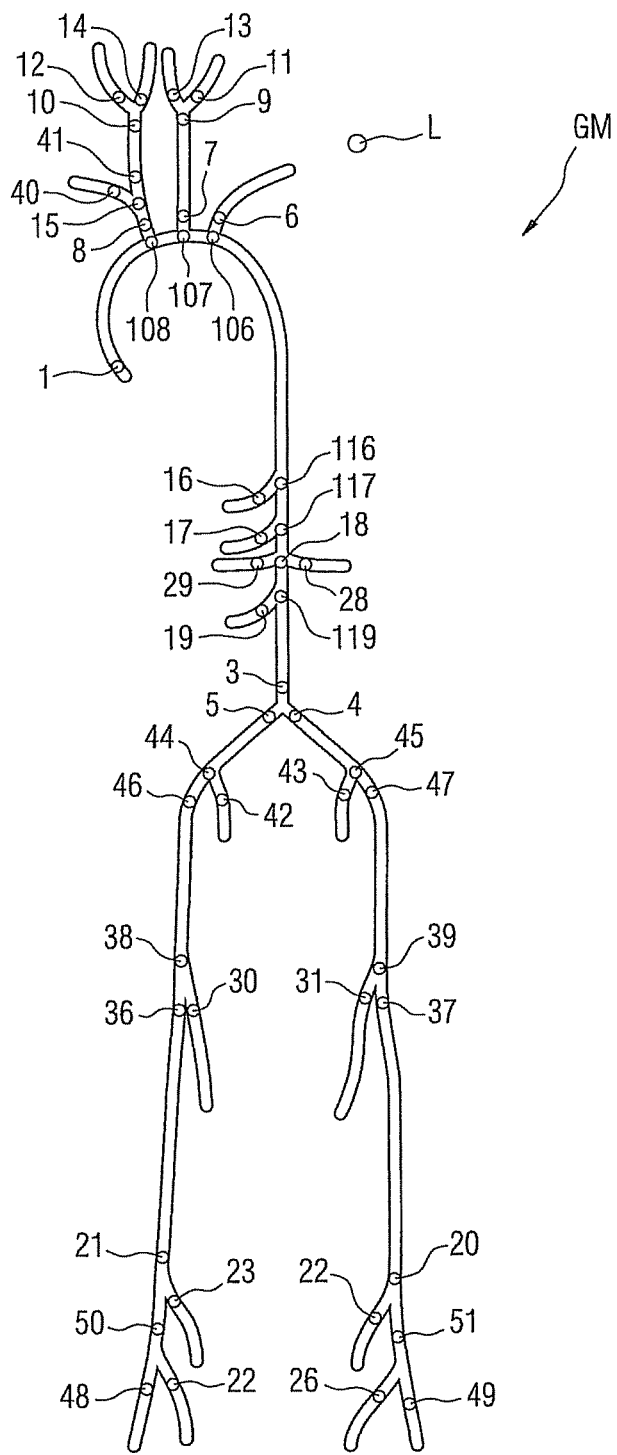
FIG. 1: shows a schematic illustration of a vessel model with landmarks and vessel connections.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Previously, the medical practitioner was assisted during the examination by being offered the option of generating vessel midlines. In order to generate the vessel midline, the examining medical practitioner had to set two or more click-points into the vessel to be examined. The vessel midline was generated automatically on the basis of said click-points. On the basis of the vessel midline, the radiologist could be offered a CPR as an overview of the state of an individual vessel. The applicant's patent application with the reference number DE 10 2009 032 257.4, the entire contents of which are hereby incorporated herein by reference which does not have a prior publication date, has already presented an approach for a fully automatic generation of the vessel midlines.

According to an embodiment of the invention, modeling of anatomical knowledge from a number of vessel trees and the extraction of the vessel tree from a present data record is based on three components:

the graph model: consisting of landmarks and vessel connections the statistical vessel model: containing anatomical knowledge from the volume of training data the vessel model: an extracted vessel model of a concrete data record The graph model contains an abstract representation of a vessel tree consisting of landmarks (nodes) with IDs 1 to 119 (ID=identification number) and their vessel connections (edges) illustrated by lines. FIG. 1 shows such a schematically visualized graph model, wherein the arrangement of the landmarks is based on the corresponding anatomical position for improved clarity. Moreover, the visualization of contained anatomical variations was dispensed with for improved clarity. The definition of the graph model preferably occurs as a result of user interaction by an expert, and it can be stored in the form of an XML file, for example. The graph model prescribes the very abstract shape of the vessel tree. This background knowledge defines the relations between possible landmarks in the form of existing vessel connections. It does not contain positions, radii or other metric variables; instead, all that is defined is a graph of possible vessel connections.

Figure 2:
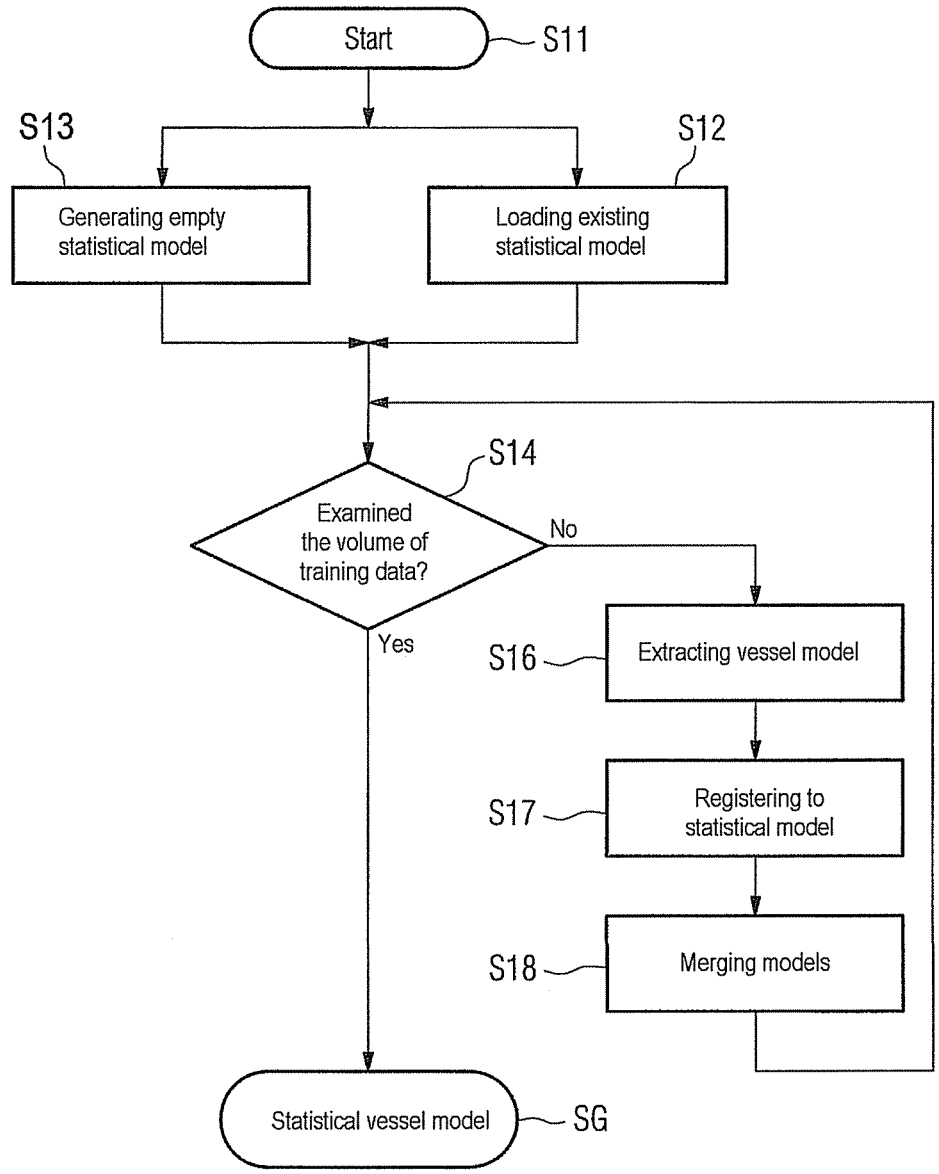
FIG. 2: shows a flowchart for generating a statistical vessel model.

A statistical vessel model additionally contains anatomical knowledge from a volume of training data. FIG. 2 illustrates, with the aid of a flowchart, how the anatomical knowledge is merged with a volume of training data and combined in a statistical vessel model.

Starting at the start in accordance with step S11, an empty statistical vessel model is first of all generated in step S13 or, if already available, an existing statistical vessel model is loaded as per step S12. Thereafter, the volume of training data is examined in step S14, wherein, if there still is data, a new vessel model is extracted in step S16, this new model is registered to the statistical vessel model in step S17 and the new vessel model is merged with the available statistical vessel model in step S18. This is iterated until the volume of training data has been examined in its entirety, wherein the new statistical vessel model SG is generated as a result.

Hence, after the training, the statistical vessel model contains anatomical information from a sufficiently large volume of data such that it can be considered representative. Thus, the vessel model of a data record constitutes a model-based description of the vessel tree. Here, the properties of each landmark and the vessel connections can be represented in the form of vectors, as n-tuples of property specifications in an n-dimensional space. Here, a registration to the statistical vessel model is carried out, starting from a subset of landmarks contained in the data record. Using the statistical knowledge, the number of landmarks is then increased iteratively, or there is an iterative extraction of the model parameters. The statistical vessel model becomes more meaningful and more reliable as the number of vessel models merged for the generation thereof increases.

The vessel model is examined following the extraction of the model parameters. Here, the information from the vessel model is examined and interpreted using the statistical vessel model. Deviations of the vessel model from the statistical vessel model may form the basis for the medical practitioner for diagnosing pathologies.

In the following text, an exemplary implementation of parts of the above-described concepts is presented:

As described above, the graph model defines an abstract view of the vessel connections between landmarks.

The following part of a configuration file illustrates a possible definition of this basic knowledge:

```
<VesselTreeModel>
    <Landmarks>
        <BodyRegion
        Name="Thorax">
            <LandMark ID="6"      Name="A. subclavia sinistra"    />
            <LandMark ID="106"    Name="Aorta --- A. subclavia    />
                                  sinistra"
            <LandMark ID="7"      Name="A. carotis communis       />
                                  sinistra proximal"
            <LandMark ID="107"    Name="Aorta --- A. carotis      />
                                  communis sinistra"
            <LandMark ID="1"      Name="Valva aortae"             />
            <!--...further
            landmarks...-->
        </BodyRegion>
        <BodyRegion
        Name="Collum">
            <LandMark ID="11"     Name="A. carotis interna        />
                                  sinistra"
            <LandMark ID="13"     Name="A. carotis externa        />
                                  sinistra"
            <LandMark ID="9"      Name="A. carotis sinus          />
                                  sinistra"
            <LandMark ID="12"     Name="A. carotis interna        />
                                  dextra"
            <LandMark ID="14"     Name="A. carotis externa        />
                                  dextra"
            <LandMark ID="10"     Name="A. carotis sinus          />
                                  dextra"
        </BodyRegion>
        <!--...further body
        regions...-->
    </LandMarks>
    <Vessels>
        <Vessel ID="0"            NODE_B="108"
        NODE_A="1"                Name="A. ascendens"/>
        <Vessel ID="1"            NODE_B="8"
        NODE_A="108"              Name="Truncus
                                  brachiocephalicus"/>
        <Vessel ID="2"            NODE_B="15" Name=
        NODE_A="8"                " A. carotis communis
                                  dextra"/>
        <!--...further vessel
        connections...-->
    </Vessels>
</VesselTreeModel>
```

The landmarks defined by this are annotated in a volume of training data records. Moreover, the connecting vessel sections with all required parameters are defined by the radiologist for this volume of training data, which serves as the basis for training the statistical vessel model.

The statistical vessel model stores statistical information that allows a precise geometric description of the landmarks and blood vessels. In the example case of landmarks, these are the following parameters:

name statistical position (location probability)

information relating to the model merging (e.g. number of merged values).

Figure 4:
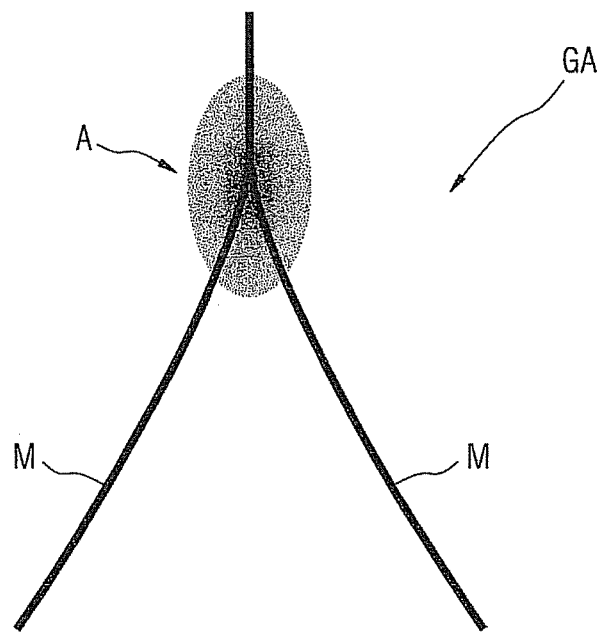
FIG. 4: shows statistical information relating to the location probability of an individual landmark.

The description of the location probability is visualized in FIG. 4. The latter shows the profile M of the midline of a vessel section GA, with a single branching, in a vessel tree, and the location probability A thereof. As this location probability A of the landmark decreases, the illustration of the point cloud becomes more transparent.

Figure 5:
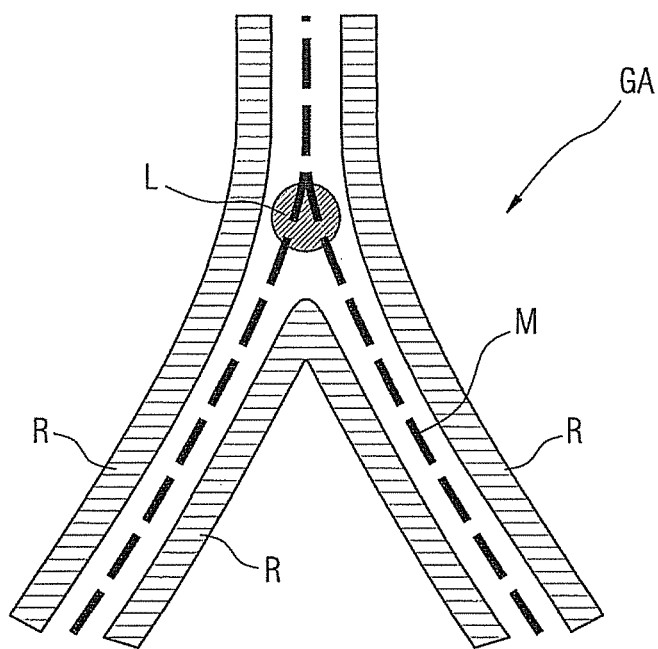
FIG. 5: shows statistical information relating to the radii around a midline of a vessel.

Representative vessel cross sections, which are orthogonal to the midline, can be used for the statistical description of the geometry of blood vessels. FIG. 5 shows a vessel section GA, with a single branching, in the vessel tree from FIG. 1, with the dashed midline M and the landmark L at the branching point of the midline M. Moreover, a simplified visualization of the profile R of the statistical radii is also shown in the case of a fixed midline M.

Moreover, the geometric description of vessel sections inter alia includes:

start/end landmark, description of the vessel profile, statistical length, list of statistical vessel cross sections, information relating to the model merging.

The information relating to the model merging describes additional parameters that are required for training and registering the statistical vessel model. A skillful selection of these variables allows the training of the statistical vessel model to be continued at a later stage, without reexamining already learnt data records. Moreover, nor is it necessary within the scope of merging to keep all vessel models in the storage medium; rather, it is possible to implement an iterative training.

The vessel model of an individual data record is similar to the statistical vessel model, but it contains no statistical variables. The required portion of landmarks for initializing the method can be defined interactively by user interaction. However, alternatively, existing fully-automatic methods are also suitable for this, as a result of which the entire architecture may be implemented as a fully-automatic method. If an initial number of landmarks are known, it is possible to register the vessel model to the statistical vessel model by an affine registration. This step allows the anatomical knowledge contained in the statistical vessel model to be used below in the examination of the data record. Thus, for example, length information of individual vessel sections can be used for targeted searching in very restricted areas for branching vessels with known geometric properties. In this respect, methods that utilize the anatomical context for examining branchings are particularly suitable. This is because, in contrast to other methods, the presented method provides comprehensive anatomical information.

After the complete extraction from the image data, the vessel model offers simple access to a wide range of parameters that can be utilized for an examination of the vessel tree. For example, entering anatomical names can access blood vessels and there can be a suitable visualization for this vessel, optionally with highlighting of the named vessel. As a result of the availability of the statistical vessel model, it is possible to visualize and examine deviations from the anatomical standard in accordance with the medical prescriptions. Moreover, this provides the radiologist with a means, by means of which it is possible in a targeted fashion to define regions that deviate from the standard and to highlight or filter out these regions.

Previous methods only use very limited anatomical knowledge for segmenting blood-vessel trees. By way of example, this can be seen by virtue of the fact that the results are not precise, particularly in branching regions. The described architecture provides the necessary anatomical background knowledge, by means of which adapted methods can be utilized for both branched and unbranched vessel sections. Moreover, the results to be expected together with the statistical information are already known at the time of the vessel segmentation or parameter extraction. This makes it possible to detect and correct erroneous results from a multiplicity of existing methods. Furthermore, interactive methods for examining a vessel are based on a manual definition of one or more seed points, which define the start/end point of the blood vessel to be examined. In contrast to the method according to an embodiment of the invention, such methods make no use of knowledge relating to the surrounding anatomy, as a result of which the robustness of these methods suffers. In other words, the inclusion of anatomical knowledge in the method according to an embodiment of the invention presented here achieves a particular robustness of the identification process.

In addition to the improved identification of blood vessels, and optionally the segmentation resulting therefrom, the architecture significantly contributes to examining the anatomy in the present data record. Starting from a small number of anatomical landmarks, there is an iteratively improved registration of the statistical vessel model to the data record. In the process, a large number of landmarks are detected in the data record, which landmarks could serve for orientation purposes in the other methods. By way of example, these can be methods for segmenting individual organs such as liver, kidneys, heart or the like.

Moreover, the statistical vessel model provides normal values or statistical ranges for the mean, which are indispensable for a meaningful interpretation of the segmentation result by the diagnosing medical practitioner. This can be used to examine vessel diameters in the anatomical context and detect pathological deviations. By way of example, this also makes it possible in a targeted and more detailed fashion to examine vessel sections, in which pathological vessel changes are found to be very common as a result of statistical observations.

The knowledge of normal statistical values and usual ranges in variations allows options for visualization that were previously unavailable. Thus, for example, the deviations of the blood vessel tree from the statistical vessel model can be displayed in a very clear fashion using a color-coded three-dimensional display, as described by e.g. the applicant's patent application with the official reference number DE 10 2009 052 315.4, the entire contents of which are hereby incorporated by reference, which does not have a prior publication date.

Figure 3:
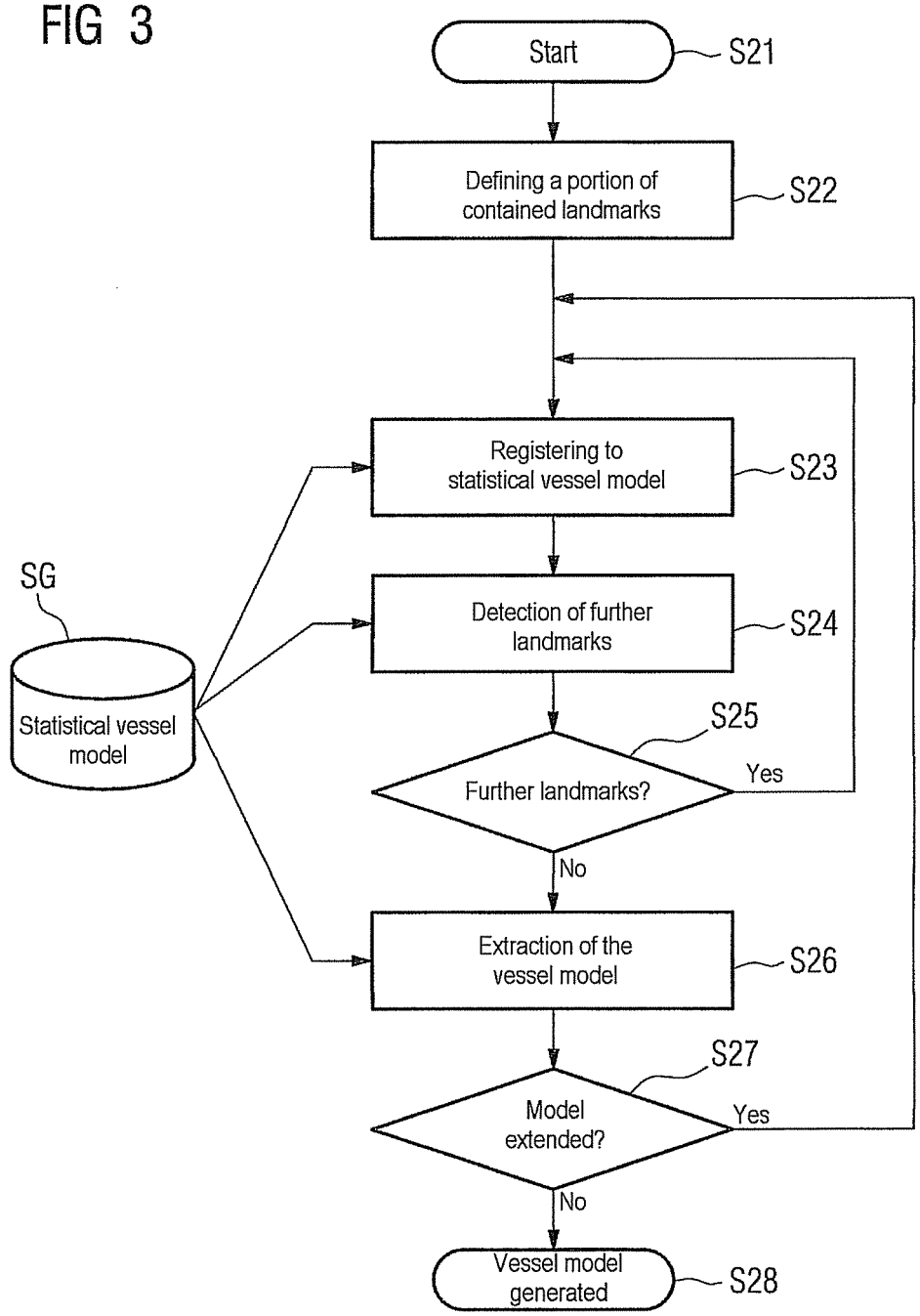
FIG. 3: shows a flowchart for extracting a vessel model using the statistical vessel model.

FIG. 3 illustrates such a method procedure according to the invention. It starts with the start S21, which is followed in step S22 by the definition of a first portion of contained landmarks. In step S23, these are registered to the selected statistical vessel model. This drastically improves the automatic identifiability of the landmarks, and so further landmarks can be detected in the subsequent step S24. Step S25 decides whether further landmarks were found. If this is the case, there is a return branch to step S23; if no further landmarks could be found, an extraction of the vessel model starts in step S26. A decision is made in step S27 as to whether the vessel model was extended as a result of the extraction. If so, there once again is a return branch to step S23. If not, the current generated vessel model is output in step S28. Additionally, it is also shown that steps S23, S24 and S26 each make use of data from the statistical vessel model SG.

In principle, the method according to an embodiment of the invention can be carried out with data records from all conventional tomographic examination methods that allow an identification of vessel structures. However, this holds particularly true for X-ray CT and magnetic resonance imaging examinations, the systems of which are shown in an exemplary fashion in FIGS. 6 to 8.

Figure 6:
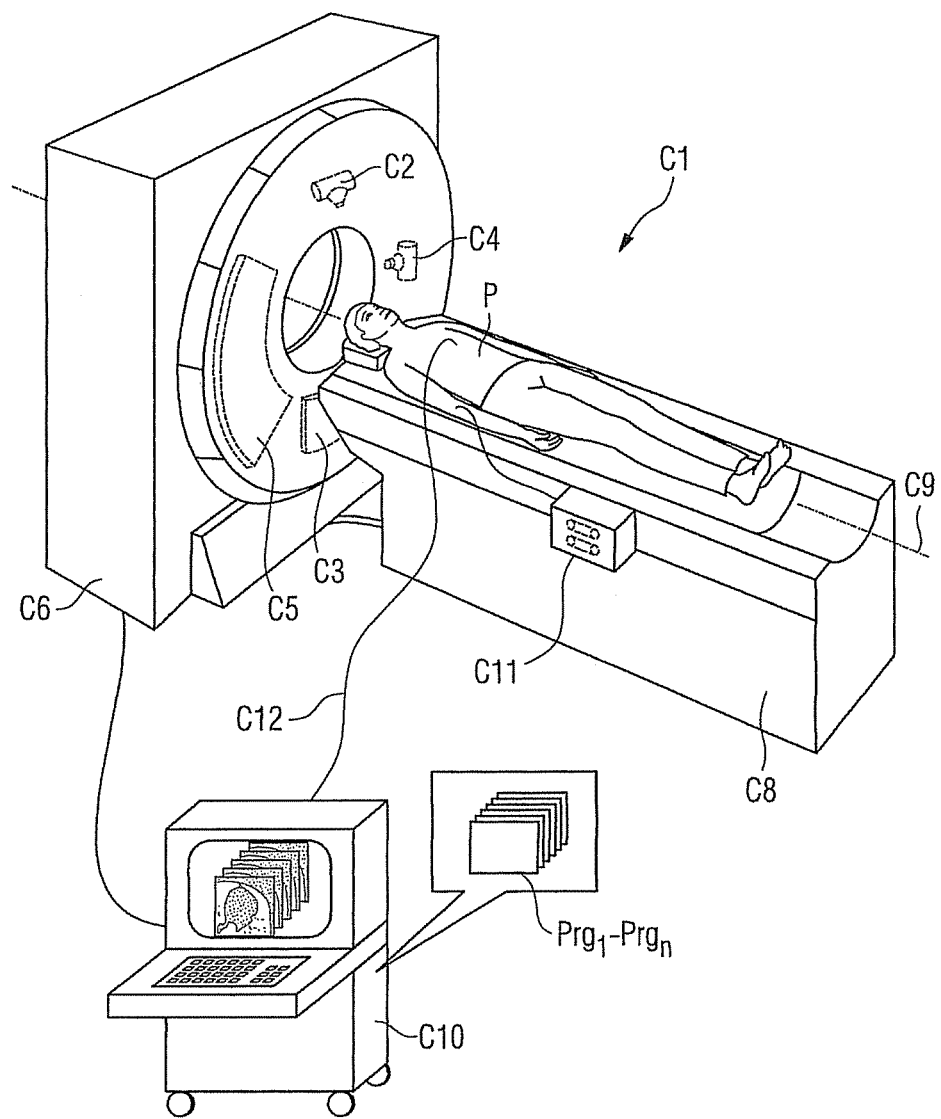
FIG. 6: shows a schematic illustration of a CT-system for carrying out the method according to an embodiment of the invention.

FIG. 6 shows a CT-system C1, by means of which the method according to an embodiment of the invention can be carried out. The CT-system C1 has a first tube/detector system with an X-ray tube C2 and an opposing detector C3. This CT-system C1 may optionally comprise a second X-ray tube C4 with an opposing detector C5. Both tube/detector systems are situated on a gantry, which is arranged in a scanner C6 and rotates around a system axis C9 during the scan. The patient P is situated on a displaceable examination couch C8, which is pushed, either continuously or sequentially, along the system axis C9 and through the scanning field arranged in the scanner C6, wherein the attenuation of the X-ray radiation, emitted by the X-ray tubes, is measured by the detectors.

During the measurement, a contrast agent bolus can be injected into the patient P with the aid of a contrast agent applicator C11; this is done so that blood vessels can be identified more easily. In the case of cardiac recordings, the cardiac activity can be additionally measured with the aid of an EKG line C12, and an EKG-gated scan can be carried out.

The CT-system is controlled with the aid of a computer system C10, which contains computer programs $Prg_1$ to $Prg_n$, which can also carry out the method according to an embodiment of the invention described above. Additionally, image data can also be output via this computer system C10.

Reference is made to the fact that the method according to an embodiment of the invention can also be carried out using computer systems that merely obtain the necessary tomographic detector data and calculate the 3D image data or directly obtain tomographic image data and carry out the method according to an embodiment of the invention using it.

Figure 7:
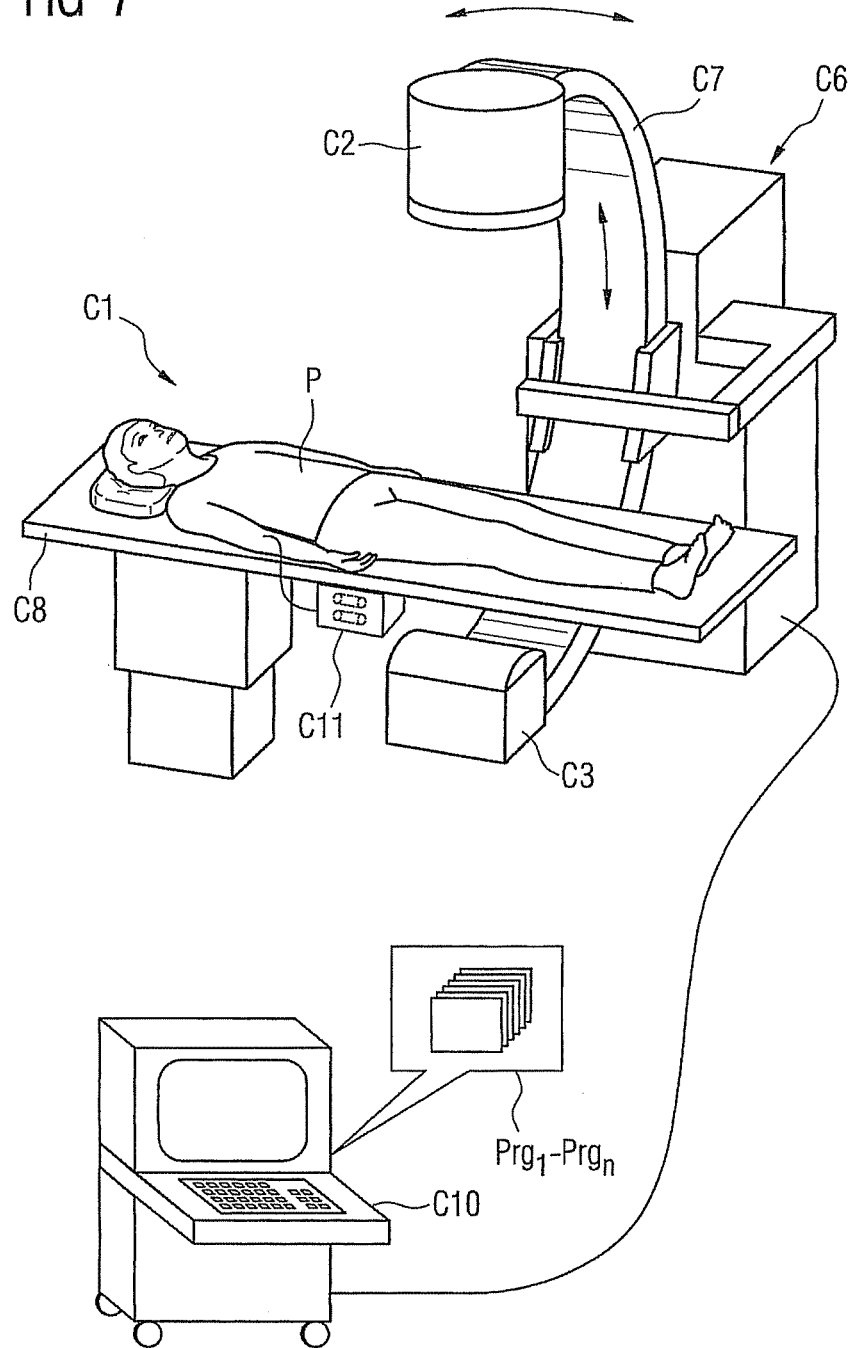
FIG. 7: shows a schematic illustration of a C-arm system for carrying out the method according to an embodiment of the invention.

This method can alternatively also be used in fluoroscopy. In this respect, FIG. 7 shows a C-arm system C1, by which fluoroscopic recordings can be generated, particularly within the scope of interventional angiographies. The C-arm system C1 illustrated here likewise comprises a scanner C6 with an X-ray tube C2 with an opposing, planar detector C3. The X-ray tube C2 and the detector C3 can be pivoted to any desired position around the patient P with the aid of a pivot arm C7. The patient P is situated on a patient couch C8, which additionally comprises a contrast agent applicator system C11 in order optionally to inject contrast agent for visualizing blood vessels. The system is controlled by a computer system C10, which has computer programs $Prg_1$ to $Prg_n$ in a storage medium thereof, which computer programs can inter alia also carry out the method according to an embodiment of the invention for image processing.

Figure 8:
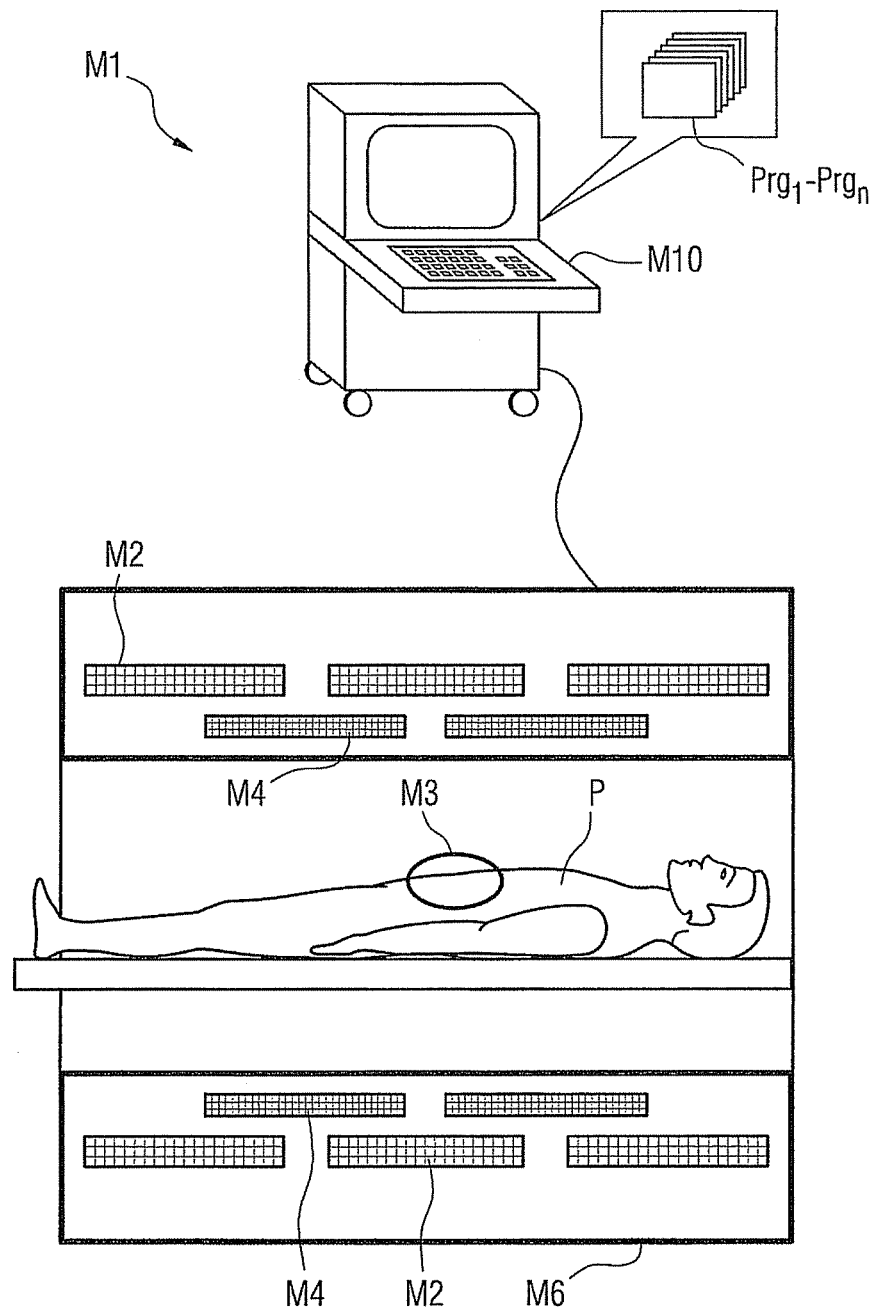
FIG. 8: shows a schematic illustration of an MRI-system for carrying out the method according to an embodiment of the invention.

Finally, FIG. 8 schematically illustrates a magnetic resonance imaging system (MRI-system) M1. Within a scanner M6 in this MRI-system M1 there are magnetic coils M2 for generating a strong main magnetic field, as a result of which the hydrogen nuclei in the body of the patient, depending on their spin, align parallel or anti-parallel to the magnetic field lines. By exciting the atomic nuclei using an alternating electromagnetic field at the resonant frequency of the atomic nuclei, the latter are prompted to oscillate. After the excitation frequency is switched off, the atomic nuclei return to their positions and emit the oscillation energy thereof in the form of electromagnetic oscillation energy, which is measured with the aid of reception coils M3. As a result of additional magnetic coils M4, a weak magnetic field with a defined field gradient is generated, as a result of which the signals emitted by the nuclei obtain spatial information, by which the position of the emitted signal may be defined. This system M1 is controlled by the computer system M10, which also evaluates the measurement signals and has programs $Prg_1$ to $Prg_n$ in its storage medium, which programs also carry out the method according to the invention in addition to the control and the image calculation.

Thus, overall an embodiment of the invention proposes a method and a device, which, firstly, carries out an automatic recognition procedure for a vessel tree in a substantially more effective fashion as a result of automatic application of previously learnt anatomical knowledge and, secondly, provides vectorized properties of a vessel tree extracted from the image data for this. As a result, on the basis of this processed data, a medical practitioner can carry out his/her diagnostic activity in a substantially more effective fashion.

It is understood that the aforementioned features of embodiments of the invention can be used not only in the respectively specified combination but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic vectorization of the profile of a vessel tree with landmarks and vessel connections connecting said landmarks with at least one property, on the basis of tomographic images of an examined patient, comprising:

providing statistically established location probabilities of landmarks in a vessel tree, in the form of a statistical vessel model, on the basis of evaluated tomographic image data records from a multiplicity of statistically comparable persons;

acquiring or generating a current tomographic image data record of the patient;

automatically determining a plurality of distinctive landmarks in the vessel tree in the current tomographic image data record of the patient;

registering the current tomographic image data record to the statistical vessel model by approximating the landmarks established in the current tomographic image data record with the corresponding landmarks in the statistical vessel model;

automatically determining previously unidentified landmarks in the registered tomographic image data record using characteristic identification features of the previously unidentified landmarks from the statistical vessel model and the statistical location probability thereof;

determining at least one current vessel model using the identified landmarks and at least one vessel property at least one of at and between the identified landmarks; and outputting the current vessel model.

2. The method as claimed in claim 1, wherein at least one iteration is carried out with repeated registration using all known landmarks and identification of new landmarks.

3. The method as claimed in claim 1, wherein the output data from the current vessel model is filtered.

4. The method as claimed in claim 3, wherein at least one predefined filter criterion is provided.

5. The method as claimed in claim 3 wherein the filtering is applied to the at least one vessel property.

6. The method as claimed in claim 1, wherein the principle of an active shape model or an active appearance model is used for the registration.

7. The method as claimed in claim 1, wherein pattern recognition is used for identifying landmarks, the pattern recognition being restricted to a region with a predefined location probability of the sought-after landmark in the statistical vessel model.

8. The method as claimed in claim 1, wherein the statistical vessel model contains at least the following parameters:
description of each landmark, and
statistical position of each landmark.

9. The method as claimed in claim 1, wherein the output vessel model contains, in addition to the landmark parameters, at least one parameter for the statistical description of the geometry of the vessel in each vessel section between two landmarks.

10. A computer system, comprising:
a scanner; and
a non-transitory storage medium to store computer programs, the computer programs carrying out the method of claim 1 when executed during operation of the computer system.

11. The method as claimed in claim 2, wherein the output data from the current vessel model is filtered.

12. The method as claimed in claim 11, wherein at least one predefined filter criterion is provided.

13. The method as claimed in claim 11, wherein the filtering is applied to the at least one vessel property.

14. The method as claimed in claim 12, wherein the filtering is applied to the at least one vessel property.

15. The method as claimed in claim 4, wherein the filtering is applied to the at least one vessel property.

16. The computer system of claim 10, wherein the computer system is a tomography system.

* * * * *